United States Patent [19]

Jackman

[11] Patent Number: 5,091,568

[45] Date of Patent: Feb. 25, 1992

[54] OXYGEN-RUTHENIUM OXIDE OXIDATION OF 2-HYDROXY-3,3-DIMETHYL-BUTANOIC ACID

[75] Inventor: Dennis E. Jackman, Prairie Village, Kans.

[73] Assignee: Mobay Corporation, Pittsburgh, Pa.

[21] Appl. No.: 867,345

[22] Filed: May 23, 1986

Related U.S. Application Data

[63] Continuation-in-part of Ser. No. 832,504, Feb. 21, 1986, abandoned.

[51] Int. Cl.$^5$ .................. C07C 51/373; C07C 59/185
[52] U.S. Cl. ...................................... 562/577; 562/525
[58] Field of Search ......................................... 562/577

[56] References Cited

U.S. PATENT DOCUMENTS 3,479,403  11/1969  MacLean ............................ 562/538
4,247,716  1/1981  Kiyoura ........................... 562/577 X

OTHER PUBLICATIONS

Ryland, Organic Synthesis with Noble Metal Catalysts, vol. 28 (1973), pp. 133-134.
Cotton et al., "Advanced Inorganic Chemistry" (third edition) Wiley, p. 846.
Silverman, Oak Ridge National Laboratory Report 746, Series A, Nov. 13, 1950, pp. 1, 2 and 7.
Trifiro, Chim. Ind., vol. 56, 1974.

*Primary Examiner*—Vivian Garner
*Attorney, Agent, or Firm*—Joseph C. Gil; Lyndanne M. Whalen

[57] ABSTRACT

In the oxidation of 2-hydroxy-3,3-dimethyl-butanoic acid in solution in the presence of a ruthenium oxide catalyst to produce 2-oxo-3,3-dimethyl-butanoic acid, the improvement wherein oxidation is effected with oxygen.

5 Claims, No Drawings

OXYGEN-RUTHENIUM OXIDE OXIDATION OF 2-HYDROXY-3,3-DIMETHYL-BUTANOIC ACID

This is a continuation-in-part of application Ser. No. 832,504, filed Feb. 21, 1986, now abandoned.

The present invention relates to an improvement in the ruthenium oxide catalyzed oxidation of 2-hydroxy-3,3-dimethyl-butanoic acid to 2-oxo-3,3-dimethyl-butanoic acid.

Organic Synthesis With Noble Metal Catalysts, Ryland, Vol. 28 (1973) pages 133–134 discloses that when oxidizing with a ruthenium tetroxide catalyst "the reactions are conducted in the presence of an oxidizing agent of sufficient strength to reoxidize the reduced ruthenium . . . Suitable oxidizing agents in alkaline media are chlorine and metal hypochlorites, whereas in acidic media bromates, permanganates, periodates, perchloric acid, sodium bismuthate, chromic acid, lead tetraacetate, and other oxidants have been used . . . "

Commonly assigned U.S. application Ser. No. 181,542, filed Aug. 26, 1980, now U.S. Pat. No. 4,614,822, discloses that 2-hydroxy-3,3-dimethyl-butanoic acid can be oxidized to 2-oxo-3,3-dimethyl-butanoic acid using sodium hypochlorite as the oxidizing agent and a ruthenium oxide catalyst. The oxidation proceeds well and in high yield. However, hypochlorite is relatively costly and is used as a solution. Accordingly, there is a greater volume of waste liquid at the end of the reaction posing disposal problems. In addition, the extra reactant volume imposes a limit on the reactor capacity.

It is accordingly an object of the invention to simplify this known process.

This and other objects and advantages have been realized in accordance with the present invention pursuant to which it has surprisingly been found that the reaction proceeds well using oxygen as the reoxidizing agent for the ruthenium catalyst.

From the state of the art it is surprising that so simple an oxidizing agent is satisfactory since for other ruthenium-catalyzed oxidations more costly, exotic re-oxidizing agents have been required.

Advantageously the instant reaction is effected in solution, preferably in aqueous solution under alkaline pH. Thus the starting acid can be in the form of a salt, e.g. an alkali metal salt, and/or alkali may be added to water along with the acid to promote its dissolution. In water, an alkaline pH of about 11 to 14, preferably about 12 to 13 is desirable.

Even if the reaction is commenced in an organic solvent some water will be present since it is a by-product of the oxidation. Steps can be taken to remove the by-product water azeotropically but this is not necessary, unless one seeks to accelerate the reaction.

The reaction desirably takes place above room temperature, advantageously from about 80° C. to 150° C. Higher temperatures require higher pressures. The oxygen may be simply bubbled into the solution to arrive at a pre-determined pressure, oxygen being added as consumed to maintain the pressure. Theoretically atmospheric pressure would even be suitable, with unused oxygen venting to the atmosphere. Advantageously pressures as high as 800 psig are suitable, preferably from about 300 to 600 psig.

The ruthenium is advantageously employed as ruthenium dioxide. It is advantageously present in about 0.1 to 5, and preferably about 0.5 to 2%, by weight of the reactant.

The oxygen is desirably in at least 50% concentration in the oxidizing gas which preferably is substantially pure oxygen.

The reaction is generally conducted batchwise. At the end of a cycle the reactor contents are separated into liquid and solids. The solid is the ruthenium catalyst which can directly be used in another cycle. The liquid is a solution containing the desired product in the form of a salt. The solution is then treated in the same manner as heretofore to recover the desired product, which can then be used in known manner as an intermediate in herbicide production.

Heretofore, metal oxides plus oxygen have been used to oxidize alcohols to ketones but surprisingly oxides of metals such as manganese, zinc, magnesium and iron do not catalyze the instant reaction to any significant extent.

The invention will be further described in the following illustrative examples wherein all parts are by weight unless otherwise expressed.

EXAMPLE 1

24 Grams (0.60 mole) of sodium hydroxide pellets were dissolved in 400 grams of a 12.1% aqueous solution of 2-hydroxy-3,3-dimethyl-butanoic acid (0.3636 mole) and quantitatively transferred to the reactor containing 0.5 gram of ruthenium oxide. The reactor head was sealed and torqued to specifications. Oxygen was introduced to the reactor to 500 psi. The reactor was stirred and heated to 80 degrees C., the temperature and agitation having been maintained for 24 hours.

The temperature rose to 95° C. and the pressure to 625 psig. After about 1.5 hours the temperature fell to and was held at 80° C., the pressure falling to 600 psig. After 24 hours at 80° C. the pressure was 475 psig. The heating and agitator were stopped. The reactor was removed from the heating well and cooled in an ice bath to ambient temperature. The pressure was 390 psig. The excess oxygen was slowly vented.

The reactor was opened and the stirrer shaft and blades rinsed with distilled $H_2O$. The contents of the reactor were quantitatively filtered through a Millipore GF/A filter paper to retain the ruthenium oxide catalyst. The catalyst was rinsed with distilled $H_2O$, then air dried.

The yield of 2-oxo-3,3-dimethyl-butanoic acid was 37.9 grams in a total solution of 549.3 grams. The conversion, or net yield, from the 2-hydroxy-3,3-dimethyl-butanoic acid was 79.5%. Also found was 4.45 grams of trimethylacetic acid and 0.275 grams of the unreacted 2-hydroxy-3,3-dimethyl-butanoic acid. The molar accountability was 92%.

EXAMPLE 2 (Comparison)

2.6 Grams of wet $MnO_2$ were charged to the Parr reactor of Example 1 with 14.5 gm NaOH pellets (0.3636 mole) and 400 gms of a 12.1% solution (0.3636 mole) of 2-hydroxy-3,3-dimethyl-butanoic acid. The reactor was sealed and pressurized to 160 psig with oxygen. The reaction was carried out at 135° C. for 20 hours.

Work-up of the reaction vessel contents gave 566 gms of solution containing 1.82% of 2-oxo-3,3-dimethyl-butanoic acid (II), 3.50% of 2-hydroxy-3,3-dimethylbutanoic acid (I) and 1.35% of trimethylacetic acid (III). The net yield or conversion of II from I was 21.8%. The molar accountability was 83.7%.

EXAMPLE 3 (Comparison)

Example 2 was repeated at 90° C. and 160 psig with 0.5005 gm of dry $MNO_2$. The reaction time was 30 hours.

Work-up of the reaction vessel contents gave 502 gms of solution containing 0.4% (II), 9.4% (I) and 0.1% (III). The net yield, or conversion of II from I was 4.2%. Molar accountability is 103%.

EXAMPLE 4 (Comparison)

$Fe_2O_3$ (0.5012 gm) was used as catalyst by adding it to the 400 gm solution of hydroxy salt containing 24 gm of added NaOH pellets (0.6 mole). The reaction conditions were 20 hours at 80° C. and 500 psig oxygen. There was little or no $O_2$ consumption—600 psig at start, 590 psig at 20 hours.

The work-up of the reaction vessel contents produced 474.5 gm of solution containing 0.42% (II); 6.01% (I) and 0.09% (III). The net yield or conversion of II from I is 4.2%. Molar accountability is 64%.

Examples 2,3 and 4 show that the oxides of manganese and iron, even though equivalent to ruthenium oxide in some other oxidations, do not perform comparably to ruthenium oxide in the instant oxidation of 2-hydroxy-3,3-dimethyl-butanoic acid with oxygen.

It will be understood that the specification and examples are illustrative but not limitative of the present invention and that other embodiments within the spirit and scope of the invention will suggest themselves to those skilled in the art.

What is claimed is:

1. In the oxidation of 2-hydroxy-3,3-dimethyl-butanoic acid in solution in the presence of a ruthenium oxide catalyst to produce 2-oxo-3,3-dimethyl-butanoic acid, the improvement wherein oxidation is effected with oxygen under alkaline conditions.

2. A process according to claim 1, wherein the oxygen is substantially pure oxygen.

3. A process according to claim 1, wherein the solution is an aqueous alkaline solution.

4. A process according to claim 3, wherein the solution is maintained under pressure and oxygen is bubbled into the solution under pressure to maintain the solution under pressure as the oxygen is consumed.

5. A process according to claim 4, wherein the pH is from 11 to 14.

* * * * *